Figure 1:
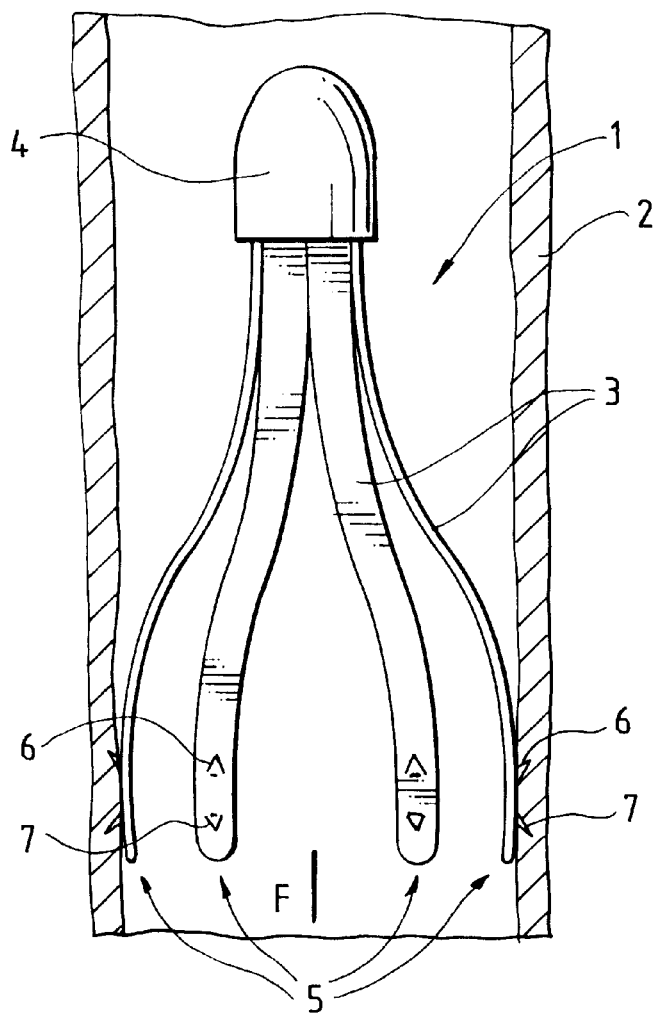

United States Patent [19]
Lefebvre

[11] Patent Number: 5,938,683
[45] Date of Patent: *Aug. 17, 1999

[54] ENDOVASCULAR FILTER WITH FLAT FIXING BRANCHES

[75] Inventor: Jean-Marie Lefebvre, Lille, France

[73] Assignee: Bentex Trading S.A., Luxembourg

[*] Notice: This patent issued on a continued prosecution application filed under 37 CFR 1.53(d), and is subject to the twenty year patent term provisions of 35 U.S.C. 154(a)(2).

[21] Appl. No.: 08/810,237

[22] Filed: Mar. 3, 1997

Related U.S. Application Data

[63] Continuation of application No. 08/522,239, filed as application No. PCT/FR95/00027, Jan. 9, 1995, abandoned.

[30] Foreign Application Priority Data

Jan. 10, 1994 [FR] France ................................ 94 00339

[51] Int. Cl.$^6$ .................................................. A61F 2/01
[52] U.S. Cl. ........................................................ 606/200
[58] Field of Search ................................ 606/200, 198

[56] References Cited

U.S. PATENT DOCUMENTS

| | | | |
|---|---|---|---|
| 3,334,629 | 8/1967 | Cohn | 128/325 |
| 5,059,205 | 10/1991 | El-Nounou | 606/200 |
| 5,234,458 | 8/1993 | Metais | 606/200 |
| 5,300,086 | 4/1994 | Gory et al. | 606/200 |
| 5,344,427 | 9/1994 | Cottenceau et al. | 606/200 |

FOREIGN PATENT DOCUMENTS

| | | | |
|---|---|---|---|
| 0350043 | 1/1990 | European Pat. Off. | A61F 2/02 |
| 0448891 | 10/1991 | European Pat. Off. | A61F 2/02 |
| 0462008 | 12/1991 | European Pat. Off. | A61F 2/02 |
| 2672487 | 8/1992 | France | A61F 2/02 |

*Primary Examiner*—Michael H. Thaler
*Attorney, Agent, or Firm*—Ladas & Parry

[57] ABSTRACT

A device for medical, use and particularly a filter intended to be placed in a vessel, provided with flat branches, called fixing branches, which cut off the blood flow when the device is placed in the vessel. The extremities of the fixing branches are locked inside of at least one ogival head by means of a locking art and the shape of said extremities is adapted to the internal and external peripheries, respectively of the ogival head and of the locking part. According to a first embodiment, the locking part and the ogival head being cylindrical parts, each fixing branch has a slightly curved extremity so as to adapt itself to the internal periphery of the ogival head and to the external periphery of the locking part. According to a second embodiment, the internal and external peripheries, respectively of the ogival head and of the locking part form regular polygons of which the number of sides is equal to the number of fixing branches of the filter, and of which the sides are parallel by pairs.

7 Claims, 2 Drawing Sheets

ENDOVASCULAR FILTER WITH FLAT FIXING BRANCHES

This is a continuation of application Ser. No. 08/522,239 filed on Dec. 12, 1995 now abandoned, which is filed as PCT/FR95/00027 filed Jan. 9, 1995.

The present invention concerns all devices intended to be placed in a provisional or definitive way in a vessel and which comprises flat branches cutting off the blood flow. It especially concerns filters preventing the migration of blood clots. More precisely, the present invention concerns the assembly there between of flat branches, called fixing branches in the present text, with which said devices are provided and which carry out the functions of filtration, the functions of fixation on the vessel wall or both these functions.

A filtering device destined to be placed in a blood vessel is known from the European patent EP.462.008 and comprises flat fixing branches which are obtained by laminating a wire made from an alloy of medical quality. These fixing branches are fixed together by soldering their extremities onto a contacting piece. When the filtering device is introduced into a vessel, the extremities of the flat fixing branches are subjected to two types of constraints, on the one hand they are subjected to a mechanical force which tends to separate them from the connecting piece and on the other hand they are subjected, on contacting the blood flow, to chemical corrosion which in time deteriates the solder points by which the extremities are fixed to the connecting piece.

These two constraints cause the extremities of the flat filter branches to become fragile during fixation at the level of each connecting piece. There is therefore a growing risk that the extremities of the filter branches will separate whereby the filter becomes inefficient and irreversible damage to the vessel wall is risked. The fragility of such a filtering device at the level of the extremities of the fixing branches harms the life time of such a device once implanted within the blood vessel.

The object of the present invention is therefore to propose a device of the type as in the European patent application EP.462.008 but which overcomes its inconveniences.

This object is perfectly achieved by the device of the invention which, conforming with the device of the European patent application EP.462.008, is destined to be placed within a vessel and is provided with fixing branches which are each formed by a broad, flat part and which cut off the blood flow when the device is placed within the vessel.

The invention is characterized in that the extremities of the fixing branches are locked inside at least one ogival head, at the level of a locking part, and in that the form of these extremities is adapted at respectively the internal and external peripheries of the ogival head and the locking part.

The main function of the ogival head and the locking part is to cause a mechanical connection between the fixing branch extremities, which is reliable and prevents all risk of separation of these extremities under the effect of mechanical forces exerted on the fixing branches of the device. As elsewhere stated, in the most general version of the device according to the invention, the extremities of the fixing branches of the device are not soldered. The invention also resolves the problem of chemical corrosion of these solder points when these come into contact with the blood flow.

In order to effect the assembling together of the fixing branch extremities of the device according to the invention at the level of the ogival head and the locking part, the extremities of the fixing branches are firstly positioned in the interior of the ogival head. Following this, the locking part is forced into the ogival head causing the extremities of the fixing branches to be locked. In theory, the locking effect is sufficiently reliable and it is not necessary to solder the extremities of the fixing branches. In practice, when carrying out this assembling operation, the introduction of the locking art causes a relative displacement of the fixing branch extremities which very slowly ride up into the interior of the ogival head. A fault in the alignment between the fixing branches results, which is detrimental to the working of the filter. In effect, when the fixing branches of such a device are in a folded up state, it is important that these are in a position perfectly parallel with each other in order to allow introduction of the device by means of a catheter into the blood vessel.

In order to overcome this problem, it is therefore preferably to solder the fixing branch extremities either directly onto the internal face of the ogival head or onto the external face of the locking part, or furthermore to solder the fixing branch extremities together along their longitudinal edges. This soldering of the fixing branch extremities has as its principal function, to avoid a displacement relative to the fixation branches on the introduction of the locking part into the ogival head. Additionally, soldering the extremities allows the dependability of the mechanical solidity of the filter to be improved. It is important to note that in this case, the ogival head and the locking part fulfill a second function which is that of protecting the solder points of the fixing extremities from the blood flow and in the same way of diminishing the risks of deteriation by chemical corrosion.

According to a first preferred embodiment of the invention, the locking part and the ogival head are cylindrical parts, wherein each fixing branch has a slightly curved extremity so as to adapt itself to the internal periphery of the ogival head and the external periphery of the locking part.

According to a second embodiment of the invention, the internal and external peripheries of the ogival head and the locking part respectively, form regular polygons of which the number of sides is equal to the number of fixing branches of the filter and of which the sides are parallel by pairs.

Figure 2:
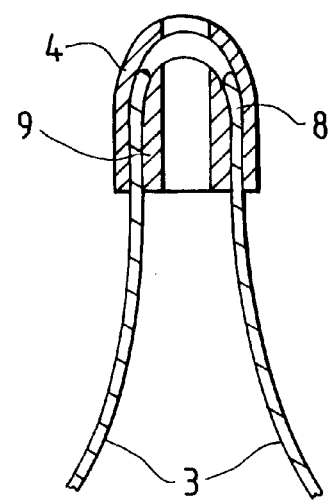
Figure 3A:
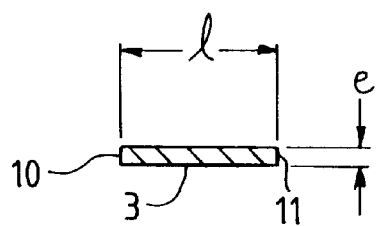
Figure 3B:
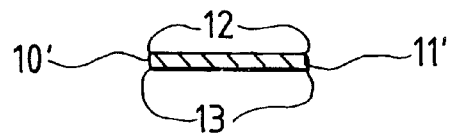
Figure 4:
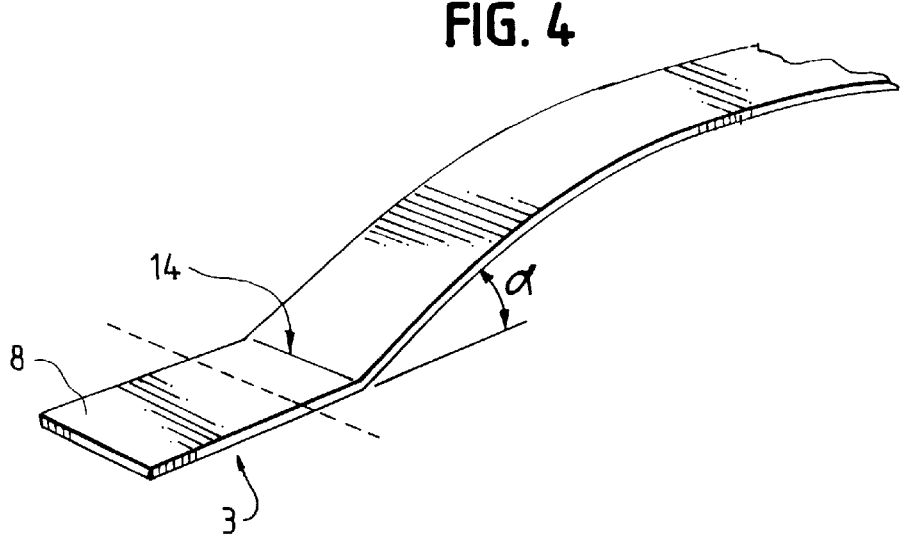
Figure 5A:
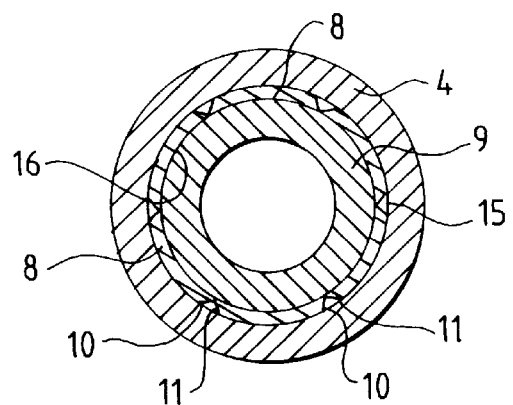
Figure 5B:
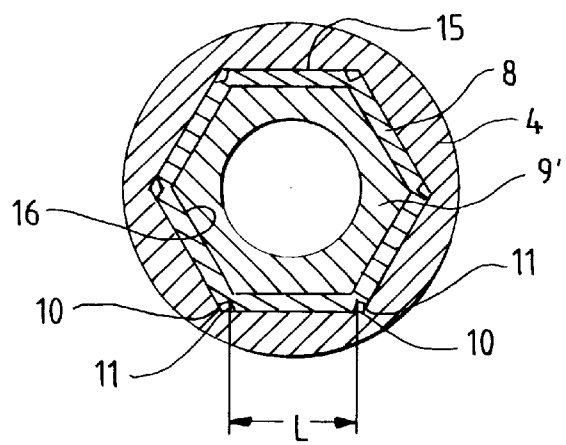

The present invention will be better understood on reading the description which refers to an example of a medical filter comprising flat fixing branches, and illustrated by the annexed drawings showing:

FIG. 1 a schematic side view of the filter within a vein;

FIG. 2 a cut away view of the filter from FIG. 1,

FIGS. 3A and 3B transferal cut away views of a fixing branch obtained respectively by flattening a round wire (FIG. 3A) and by cutting a metallic plate (FIG. 3B), FIG. 4 a partially perspective representation of a fixing branch with an angular fold, FIG. 5A a transverse cut away section of the head of a filter wherein the fixing branches have been curved along their length, and FIG. 5B cut away transverse view of the head of a filter wherein respectively the internal and external peripheries of the ogival head and of the locking part are hexagonal.

A filter 1 is represented in FIG. 1 when in position within the interior of a view 2 wherein blood flows in the direction of arrow F. Filter 1 has a generally conical form, with the fixing branches 3 being fixed to an ogival head 4. The free extremities 5 of each fixing branch have a rounded end and comprise pointed teeth 6 and 7 arranged in an antagonistic way according to the general direction of the branch.

Each branch 3 is made up of a flat strip of which the distal extremity 8 is locked in position within the interior of the ogival head by a cylindrical locking part 9 (FIG. 2).

Preferably, filter 1 comprises six lateral branches 3 which are symmetrically disposed and arranged side by side on the internal periphery of the ogival head 4 and locked into position by introduction of the locking part 9.

In order to make a branch 3, a metallic wire having a circular section is subjected to a flattening operation by heat crushing.

It will be understood that under these conditions, the longitudinal edges 10, 11 of the branch 3 have a rounded form (FIG. 3A).

Transverse sections of respectively the two fixing branches 3 are represented in FIGS. 3A and 3B: the first (FIG. 3A) is obtained by crushing a metallic wire according to the patent application EP.462.008 whilst the second (FIG. 3B) is obtained by simply cutting a metallic plate according notably to the teaching of the document FR 2 570 288. In the latter it will be noticed that the longitudinal sides 10', 11' comprise spined edges 12, 13.

During the flow of blood into the interior of the vessel 2, the fixing branches serve as the filter for blood clots. However in the case where these branches 3 have spined edges 12, 13 such as in the filter described in the document FR 2 570 288, it is remarked that under certain conditions blood clots form even in the presence of these edges 12, 13.

This phenomenon is totally unobserved when the lateral sides 10, 11 of the fixing branches have a rounded form such as shown in FIG. 3A.

The principle of hooks 6, 7 situated at the free extremities 5 of the branches 3 is known from the document FR 2 660 189 whose teaching is an integral part of the present invention.

Advantageously, each hook 6, 7 is obtained by cutting and forming a V-shape in the central zone of the free extremity 5 of each branch 3. The fact that the formation of the hooks is conducted by cutting does not yield the inconvenience wherein the hooks fix themselves into the vessel 2 and are therefore not placed permanently within the blood flow.

In the precise embodiment, each fixing branch 3 has a width L in the order of 2 mm and a thickness in the order of 0.2 mm. This is obtained by flattening a metallic wire yielding a transverse section with a diameter in the order of 0.7 mm.

Following flattening, the metallic strips obtained are preformed and thermically treated in order to have in a normal state, a curved β-form such as is shown in FIG. 1.

It will be understood that during the flattening operation of the metallic wire, the obtained flattened strip constitutes a fixing branch possessing, in a certain sense, the same quality as a laminated metallic plate. It therefore ensures that during the preforming operations destined to impart the required form to the flat strip for its utilization as a fixing branch in the device for medical use according to the invention, the flattened strip always has the same orientation. Hence any risks of asymmetry are obviated.

In order to place the filter from FIG. 1 in within a vein, it is guided by a catheter. The presence of blood within the catheter induces, of necessity, a fibrin network which envelops the filter and hinders expansion of the fixing branches 3. It is necessary that the filter can open itself so that the fixing branches are able to carry out their filtering function and equally that the pressure exerted on the venal walls by the fixing branches 3 is sufficient to allow the anchoring of the filter within this wall be means of the hooks 6,7. If this force is wished to be increased, it is necessary, taking into consideration the S-curve of the branches 3 of filter 1, to utilize the strips of which the thickness is very important, since this poses an obstruction problem when the filter is folded. It is imperative that this obstruction is minimal. As a consequence, in order to obtain the goal of a better opening of the filter during its release from the catheter and to improve the force exerted by the fixing branches on the venal wall without increasing the thickness of the metallic strips used, each fixing branch 3 is subjected, following flattening to a mechanical folding treatment in order to realize an angular fold 14, of angle α, in a proximal zone of its distal extremity 8 such as is shown by FIG. 4. In a specific example, angle α approaches roughly 30°. This angular fold 14 confers onto the fixing branch 3 a supplementary releasing effect. In FIG. 4, a schematic dotted line shows the limit of the ogival head 4, when the distal extremity 8 is locked into position there within.

In a particular first working mode, each fixing branch 3 is subjected, before introduction into the interior of the ogival head 4, to a mechanical pressing treatment destined to provide it with a gentle curve along its length, at least towards its distal extremity 8. This particular disposition allows positioning of the distal extremities 8 of all of the fixing branches 3 next to each other on entering the filter 1 arrangement following the internal periphery 15 of the ogival head 4 and following the external periphery 16 of the cylindrical part of the lock 9 (FIG. 5A).

By a second particular working mode illustrated in FIG. 5B, the internal 15 and external 16 peripheries respectively of the ogival head 4 and of the locking part 9' are regular polygons, in this case hexagons, of which the number of sides is equal to the number of fixing branches 3 of the filter. More particularly, the width L of one side of the external periphery 16 of the locking part 9' is equal to the width of each fixing branch 3; the ogival head 4 and the locking part 9' are positioned respectfully to each other in such a way that the sides of respectively their internal 15 and external 16 peripheries are parallel by pairs.

Preferably, in the two particular working modes from FIGS. 5A and 5B, when the distal extremities 8 of the fixing branches are positioned within the interior of the ogival head 4, a laser welding operation is carried out on the distal extremities 8 therebetween, prior to placing in position of the locking part 9, 9', by means of their longitudinal sides 10 and 11.

Hence, on carrying out positioning of the locking part 9, 9', all risk of displacement of the fixing branches with respect to the external periphery of the locking part 9, 9' is obviated. The fixing branches therefore, do not have the tendency to ride up during assembly, and the filter 1 therefore remains perfectly symmetrical.

The present invention is not limited by the working modes which have been exhaustively described. In particular the device for medical use can comprise a number of different fixing branches. It is conceivable within the scope of the invention to effect an automatic centering filtering device similar to that in the European patent application EP.462.008. In this case, two ogival heads are utilized, and two locking pieces for assembling the two extremities of each fixing branch of the filter with the corresponding extremities of the other fixing branches. Finally soldering of the fixing branches can be effected on the internal or external face respectively of the ogival head or the locking part.

I claim:

1. A device for medical use intended to be placed in a blood vessel, said device comprising at least one ogival shaped head having an internal periphery, a plurality of fixing branches, each of which is formed by a broad, flat part, said branches being adapted to filter blood flow when the device is placed in a blood vessel, and a locking part having an external periphery for locking the inner extremities of the fixing branches inside said ogival head, such that said extremities of the fixing branches are arranged side-by-side and are formed to correspond respectively to the shape of the internal periphery of the ogival head and the external periphery of the locking part, wherein the internal and external peripheries of the ogival head and the locking part form respectively regular polygons of which the number of sides is equal to the number of fixing branches, and which sides are parallel by pairs between the internal periphery of the ogival head and the external periphery of the locking part, wherein the extremities of the fixing branches are directly joined together in contact along their longitudinal edges on the side of the internal periphery of the ogival head.

2. A device for medical use intended to be placed in a blood vessel, said device comprising at least one ogival shaped head having an internal periphery, a plurality of fixing branches, each of which is formed by a broad, flat part, said branches being adapted to filter blood flow when the device is placed in a blood vessel, and a locking part having an external periphery for locking the inner extremities of the fixing branches inside said ogival head, such that said extremities of the fixing branches are arranged side-by-side and are formed to correspond respectively to the shape of the internal periphery of the ogival head and the external periphery of the locking part, wherein the internal and external peripheries of the ogival head and the locking part form respectively regular polygons of which the number of sides is equal to the number of fixing branches, and which sides are parallel by pairs between the internal periphery of the ogival head and the external periphery of the locking part, wherein the extremities of the fixing branches are directly joined together in contact along their longitudinal edges on the side of the external periphery of the locking part.

3. The device according to claim 1 or 2, wherein the locking part and the ogival head are generally cylindrical parts, each fixing branch having a slightly curved extremity so as to adapt itself to the internal periphery of the ogival head and to the external periphery of the locking part.

4. The device according to claim 1 or 2, wherein the width of one side of the external periphery of the locking part is equal to the width of a fixing branch.

5. The device according to claim 1 or 2, wherein each of said fixing branches includes an angular bend at an angle $\alpha$ in a proximal zone near its extremity.

6. The device according to claim 1 or 2, wherein each fixing branch is formed from a long, flat part having curved longitudinal edges.

7. The device according to claim 1 or 2, wherein each fixing branch is formed from a long, flat part obtained by flattening a metallic wire with a circular cross-section.

* * * * *